United States Patent [19]

Khalil et al.

[11] Patent Number: 4,524,787
[45] Date of Patent: Jun. 25, 1985

[54] HAIR RELAXER

[75] Inventors: Ezzat N. Khalil, Oak Park; Ernest Cheslow, Glencoe, both of Ill.

[73] Assignee: Johnson Products Co., Inc., Chicago, Ill.

[21] Appl. No.: 398,691

[22] Filed: Jul. 20, 1982

[51] Int. Cl.³ .............................................. A45D 7/00
[52] U.S. Cl. .......................................... 132/7; 424/70
[58] Field of Search ...................... 132/7; 424/70–72, 424/89

[56] References Cited

U.S. PATENT DOCUMENTS

| | | | |
|---|---|---|---|
| 4,237,910 | 12/1980 | Kahil | 132/7 |
| 4,314,572 | 2/1982 | De la Guardia | 132/7 |
| 4,390,033 | 6/1983 | Khalil | 132/7 |
| 4,416,296 | 11/1983 | Myers | 132/7 |

Primary Examiner—Gregory E. McNeill
Attorney, Agent, or Firm—Dressler, Goldsmith Shore, Sutker & Milnamow, Ltd.

[57] ABSTRACT

A hair relaxing system, activator and methods of use and preparation are disclosed. The system includes a first package containing a substantially water-free activator that includes a hydrolyzable organic base having a $PK_a$ value of at least about 12 present in free base form in an amount sufficient to relax hair dissolved in an organic solvent that is immiscible with petrolatum. The second package of the system contains water and may also contain oleaginous materials and emulsifiers. Admixture of the first and second packages provides a relaxer composition that has a pH value of at least 12 and contains at least about 20 weight percent water.

31 Claims, No Drawings

HAIR RELAXER

DESCRIPTION

1. Technical Field

This invention relates to the straightening or relaxing of human hair, and more particularly to hair relaxation utilizing a hydrolyzable organic base that is supplied in a relatively stable form.

2. Background Art

Aqueous alkali-containing hair relaxing or straightening compositions are known in the art. Such compositions usually have a pH of about 12 to 14 due to the presence of a water-soluble alkali or alkaline material such as sodium hydroxide, and are most frequently formulated as emulsified or creamy, viscous preparations so that once applied to the user's hair, they will not drip onto the skin or into the eyes.

Hair relaxers are generally supplied as "with base" or "no-base" formulations. A "with base" formulation is generally supplied in two packages; one containing the oleaginous base and one containing a thickened aqueous composition of alkaline materials. For these products with a separate oleaginous base, the base is first applied as a protective layer to the user's scalp and hair followed by application of the thickened aqueous alkaline material which then relaxes the hair. "No-base" formulations are one package systems in which the aqueous and oleaginous materials are co-emulsified. The "no-base" formulations are applied directly to the user's hair without a prior treatment of the scalp.

More recently, the usually used inorganic base, such as sodium hydroxide, has been replaced as the alkalizing agent by guanidine or its hydrate, guanidinium hydroxide, also known as guanidine hydroxide, in that these alkaline materials are said to provide improved scalp condition during and after relaxation. Guanidine and its hydrate are not, however, stable in aqueous solution, and hydrolyze to urea and its hydrolysis products on aging for only a few days.

Several methods have been disclosed for utilizing guanidine or its hydrate while seeking to avoid the problems associated with guanidine hydrolysis. U.S. Pat. Nos. 4,304,244 and 4,324,263 disclose the use of guanidine and its hydrate that are prepared and used within about 48 hours of their preparation. The principle method of guanidine preparation disclosed in those patents is the reaction of a water-soluble salt of guanidine with a water-soluble inorganic hydroxide in water to form a relatively water-insoluble inorganic salt and guanidine free base in water; i.e., guanidine hydrate. Guanidine carbonate and calcium hydroxide are said to be particularly useful for this purpose in that calcium carbonate is formed.

The formation of a relatively insoluble salt such as calcium carbonate can however lead to some problems. Thus, when the two components, calcium hydroxide and guanidine carbonate, are mixed to form a relaxing composition, the calcium carbonate precipitates in the relaxing composition. The presence of the precipitate causes the relaxing composition to have a pasty character and leads to difficulties in rinsing the relaxing composition from the hair once relaxation is completed and also to the possibility of leaving some of the precipitate on the hair or scalp as unsightly particles that appear to be dandruff.

Another problem that can arise with calcium hydroxide-containing relaxers is that the emulsion containing calcium hydroxide can partially dry, and skin over due to the formation of a solid calcium compound on surface of the emulsion. Effective sealing of the emulsion container can solve this problem, but leads to an increased product cost.

If a three component system, e.g., oleaginous base, calcium hydroxide and guanidine carbonate, is used wherein the calcium hydroxide and guanidine carbonate are first admixed with water and the resulting composition is then admixed with the oleaginous base, still further problems ensue. Here, if all three components are simply admixed, the problems of pastiness and washout discussed above are still present, along with the necessity of using and mixing three, rather than two, components.

In addition, it is stated in Examples 23-31 of U.S. Pat. No. 4,324,263 that about one to about 42 minutes can be required for equilibrium to be reached between the reactants in the system; i.e., a constancy of pH value is reached, before the solution may be used to relax hair. Having to wait for such times can also be a problem with these systems.

If instead, sufficient time is allowed to pass for the formation of a requisite amount of guanidine and the precipitated calcium sulfate, the aqueous solution of guanidine and guanidine hydrate can be separated from the precipitate by fitration or decantation. This separation step can be costly and/or time consuming, and in either event is inconvenient.

Further methods of preparing guanidine and guanidine hydrate are illustrated in U.S. Pat. Nos. 4,303,085 and 4,314,572 wherein a hydroxide form of a particulate anion exchange resin is utilized to form an aqueous solution of guanidine hydrate. Here again, the prepared guanidine must be utilized relatively quickly lest it hydrolyze.

In addition, there is an obvious problem of having to separate the guanidine solution from the resin prior to use so that the resin is not present when the relaxer is applied to the head. When the resin is present as the relaxer is placed on the head, scalp irritation from the resin particles could result, as could sink drain blockage from repeated usage and rinsing.

A still further problem with the use of an ion exchange resin for the preparation guanidine hydrate is that the required, hydroxide form of most available resins is not sufficiently stable on aging to permit their incorporation into a product. Thus, the use of an exchange resin to prepare guanidine hydrate is not believed to be a commercially acceptable method for use in a relaxer product.

Thus, it is seen that although the use of a guanidine as the alkali in hair relaxing compositions can be beneficial, that use also leads to several drawbacks from the standpoints of cost and ease of use. The present invention maintains the benefits of the use of a hydrolyzable base such as guanidine, while lessening or obviating the detriments of that use described above.

SUMMARY OF THE INVENTION

The present invention relates to a hair relaxer system having at least two portions or packages, its method of use, a method for forming a hair relaxer composition using that system, as well as an activator that can comprise the contents of one of the packages of the hair relaxer system.

The relaxer system comprises a first package containing a substantially water-free activator that includes a hydrolyzable organic base having a p$K_a$ value of at least about 12 that is dissolved in an organic solvent. The organic base is present in the activator in an amount sufficient to relax hair and the organic solvent is immiscible with petrolatum at about 25° C. The second package contains water. Admixture of the contents of the first and second packages forms a relaxer composition having a pH value of at least about 12 that contains at least about 20 weight percent water.

A particular substantially water-free activator comprising one of the ingredients of the hair relaxer system is a composition that includes a hydrolyzable organic base having a p$K_a$ value of at least about 12 that is dissolved in a polyhydroxy lower alkane. When admixed with at least about 20 weight percent water, a relaxer composition is formed which has a pH value of at least about 12 and contains a sufficient amount of the organic base to relax hair.

The system is used to relax hair by admixing the components of the first and second packages to form the relaxer composition, applying the relaxer composition to contact the hair, applying a longitudinal strain upon the hair while in contact with the relaxer composition, and maintaining the strain and contact for a time sufficient to relax the hair. The relaxer composition is thereafter removed from the hair.

The present invention and its use have several benefits and advantages.

One advantage is that the relaxer composition formed from use of the relaxer system contains no water-insoluble precipitate and is therefore free from the pastiness that is usually observed with relaxer compositions that contain such a precipitate.

Another advantage of the present invention is that the organic base is stable for practical purposes in solution in the organic solvent of the activator thereby permitting preparation and sale of a commercial product as compared to a laboratory curiosity that embodies the invention.

Yet another advantage of the present invention is that its use leaves the hair with improved sheen compared to hair treated with a commercially available product prepared from guanidinium carbonate and calcium hydroxide.

One of the benefits of the invention is that the relaxer composition rinses more easily from relaxed hair than does a relaxer that contains a water-insoluble precipitated salt such as calcium carbonate.

Another benefit of the present invention is that skinning of the emulsion is eliminated as no calcium hydroxide or similar compounds need be present therein.

Still another benefit of the present invention is that solid calcium hydroxide does not have to be incorporated into the product which facilitates production on a commercial scale.

Still further advantages and benefits will be apparent to those skilled in the art from the description, examples and claims which follow.

DETAILED DESCRIPTION OF THE INVENTION

The present invention relates to compositions and methods for relaxing or straightening human hair. Straightening by relaxation utilizes different chemistry than does straightening by so-called "reductive" methods. In relaxation, a composition having a pH value of about 12 or more is applied to the hair to break the hair keratin cystine disulfide bonds and form hair keratin that contains lanthionine. On the other hand, in reductive hair straightening, a composition is used that has a pH value between about 6 and about 10 along with a reducing agent such as a thiol, bisulfite ion or hydride ion. The reducing agent is thought to at least partially split cystine disulfides into cysteine groups which are later reformed into cystine disulfides.

The present invention is based in part upon the finding that organic bases having p$K_a$ values of at least about 12 and hydrolyze in water at ambient temperature and pressure can be made stable and useful in relaxer compositions when dissolved in an organic solvent to form an activator that contains substantially no water. These bases are referred to herein as "hydrolyzable organic bases".

The hydrolyzable bases useful herein each contain a carbon atom that is (a) doubly bonded to a nitrogen atom (an imino-bonded carbon atom) and (b) singly bonded to another nitrogen atom. The remaining carbon atom valence can be taken up by another cabon atom or another nitrogen atom, in which cases the organic base is an acetamidine or a guanidine, respectively. These hydrolyzable bases are soluble in water in their free base and/or hydrated forms.

The hydrolyzable organic bases of this invention can be contrasted structurally with non-hydrolyzable strong bases such as 1,8-bis-(dimethylamino)naphthalene and 4-dimethylaminopyridine neither of which will hydrolyze in water at 25° C. and at a pH value about equal to the base's p$K_a$ value to an extent of at least about 5 percent after about 2 days, nor contain an imino bonded carbon atom that is also singly bonded to another nitrogen atom, nor has a p$K_a$ value of at least about 12. The present organic bases can also be contrasted structurally with the tetraalkylammonium hydroxides which possess equal or superior base strengths to the hydrolyzable organic bases used in this invention, but lack the imino-bonded carbon atom that is also bonded to another nitrogen atom.

Exemplarly, useful hydrolyzable organic bases related to guanidine include, but are not limited to, guanidine itself, and guanidine substituted with 1 to 5 substituents selected from the group consisting of lower alkyl, carboxy lower alkyl, hydroxy lower alkyl, amino, lower alkyl substituted amino groups and mixtures thereof, such as N-methylguanidine, N,N'-dimethylguanidine, N,N',N''-trimethylguanidine, pentamethylguanidine, guanidine acetic acid, N-2-hydroxyethylguanidine, aminoguanidine and N-methylaminoguanidine. Exemplary, useful hydrolyzable bases related to acetamidine include, but are not limited to acetamidine, and acetamidine substituted on the carbon atom with a substituent selected from the group consisting of lower alkyl, amino, lower alkyl substitued amino groups and mixtures thereof, such as methylacetamidine, aminoacetamidine and dimethylaminoacetamidine.

As noted before, a hydrolyzable organic base useful herein has a p$K_a$ value of at least about 12. In more preferred practice, the hydrolyzable organic base has a p$K_a$ value of at least about 13.

The p$K_a$ values used herein and in the claims are values that are reported as being measured for the conjugate acids of the useful free bases, although it is the free base and/or hydrated free base forms of the hydrolyzable organic bases that is used herein for relaxing hair. For example, according to the *Handbook of Bio-*

*chemistry*, second ed., 1970, published by The Chemical Rubber Co. of Cleveland Ohio, at page J-221, the $pK_a$ value for the conjugate acids of acetamidine, dimethylaminoacetamidine, guanidine and pentamethylguanidine are reported as 12.52, 13.4, 13.6 and 13.8, respectively.

The hydrolyzable organic base of the present invention is the agent that is believed to principally, if not wholly, cause hair relaxation to occur. The source of hydrolyzable organic base with which to carry out relaxation is the substantially water-free activator.

The hydrolyzable organic base is dissolved in an organic solvent to form an activator that is substantially free of water. The organic solvent of the activator is immiscible with petrolatum at 25° C., and is preferably miscible with water at 25° C. Exemplary organic solvents include normally liquid alcohols, such as those discussed below, normally liquid amides, such as methylformamide and dimethylformamide, and the like.

Alcohols that are liquid at 25° C., and are immiscible with petrolatum at 25° C. and miscible with water are preferred organic solvents. Of the alcohols, mono- and polyhydric lower alcohols such as ethanol, 2-propanol, ethylene glycol, propylene glycol, and the like are particularly preferred. The particularly preferred mono- and polyhydric lower alcohols include the polyhydroxy lower alkanes, which are most particularly preferred solvents. Polyhydroxy lower alkanes are illustrated by ethylene glycol, propylene glycol, glycerin and 1,4-butanediol. Additional useful solvents for the hydrolyzable organic base include, but are not limited to, the lower alkanol amines such as ethanolamine, di-isopropanolamine and triethanolamine, benzyl alcohol, polymeric ethylene oxide adducts of ethylene glycol that contain an average of about 2 to about 12 polymerizedethylene oxide units per molecule, the liquid hydroxyl-terminated polyoxyethylene-polyoxypropylene-polyoxyethylene block polymers sold under the trademark PLURONIC by BASF-Wyandotte, such as PLURONIC L-121 that is reported to contain an average of 6 oxyethylene groups on either side of polyoxypropylene block containing an average of about 67 oxypropylene grups, and mixtures thereof.

A particular substantially water-free activator of this invention contains an organic base, as discussed before, dissolved in a polyhydroxy lower alkane. This activator forms a relaxer composition having a pH value of at least about 12 and contains a sufficient amount of organic base to relax hair when admixed with sufficient water to constitute at least 20 weight percent water in the relaxer composition.

The word "lower" used in conjunction with the words "alkyl" "alcohol" and/or "alkane" is meant to include carbon chains having 1 through 4 carbon atoms. It is understood that polyhydroxy lower alkanes start with ethylene glycol, there being no stable polyhydroxy derivative of methane.

The amount of hydrolyzable organic base useful in the activator is that amount of organic base in free base form which upon admixture of the activator with water will provide an amount of the organic base in the resulting relaxer composition sufficient to relax hair, with the relaxer composition containing at least about 20 weight percent water. The amount of hydrolyzable organic free base in the activator is also a function inter alia, of the rate at which relaxation is desired to be carried out and the amount of hair to be relaxed.

For completely relaxing an entire head of hair; i.e. about 50 to about 70 grams of hair, with a time for relaxation of about 20 to about 30 minutes, an activator of this invention preferably contains about 0.1 to about 0.3 moles of the organic base in free base form. For relaxation times less than about 20 minutes, the activator can contain up to about 1 mole of organic free base, while about 0.05 moles, or fewer, of the organic free base can be present in an activator for a composition designed to relax hair in more than 30 minutes, based upon complete relaxation of a whole head of hair.

Amounts of organic free base in the activator less than about 0.05 moles can be used for relaxing less than a whole head of hair or for achieving less than complete relaxation of a whole head of hair, although when used on a whole head of hair, complete relaxation tends to take too long to accomplish. Similarly, amounts in excess of about 1 mole of organic free base in the activator can be used for more rapid treatment times, but usage at such concentrations tends to be wasteful of the organic free base and the amount and rate of relaxation can be difficult to control.

Since the hydrolyzable organic base present in the relaxer composition has its source in the activator, the number of moles of organic base in the relaxer composition is initially at least as great as that present in the activator.

The hydrolyzable organic base in the relaxer composition is present in that composition primarily, if not exclusively, in the hydrated form since the organic free bases useful herein hydrate rapidly in water. The presence of small amounts of water in the substantially water free activator will convert some of the hydrolyzable organic base therein to the hydrate.

While it is believed that the hydrated form of the hydrolyzable organic base of the relaxer composition actually relaxes the hair, the amount of organic base in the activator that is sufficient to relax hair is measured as the free base because any hydrated hydrolyzable organic base present in the activator may hydrolyze therein. Thus, while it is not preferred, the total amount of hydrolyzable organic base (free base plus hydrate) may be in great excess over the amount of organic free base that is sufficient to relax hair, such as the amounts discussed hereinbefore. A large excess of total hydrolyzable organic base over the amount of the free base form is to be avoided if only because of the economic waste involved.

The activator solution useful herein is substantially free of water. Nevertheless, small amounts of water may be present in the activator. When present, the small amount of water will be present as combined water converting the free base guanidine, for example, to guanidinium hydroxide, which is unstable and converts to urea and ammonia on standing. Thus, as noted above, the activator contains a sufficient molar excess of organic free base over water so that the free base remaining will be in sufficient amount to effectively relax the hair when combined with the water-containing composition. The molar excess of organic free base over water is suitably at least about 70 mole percent.

Amounts of water as high as about 50 mole percent, or more, of the amount of free base may be present without loss of activity, but the total amount of free base required to produce the necessary excess thereby may be uneconomical.

In addition, the urea decomposition product produced by the water may constitute a problem through overtreatment of the hair. For example, when guanidinium hyroxide decomposes to urea and ammonia, the urea can act as a swelling agent for the hair and accelerate the action of the relaxer. Small amounts of urea decomposition product, or even deliberately added urea, may be beneficial; but at a level of about 1 percent of urea in the final mixed product applied to the hair there is a danger of overprocessing and an operator would have to compensate for possible overprocessing by shortening the exposure time. It is therefore preferred to limit the water content in the activator to a level not higher than about 5 weight percent of the weight of guanidine so that there will not be excessive accumulation of urea in the final product.

The second package or portion of the relaxer system of this invention contains water in an amount sufficient to provide at least about 20 weight percent water, and more preferably at least about 30 weight percent water to the relaxer composition that is formed by admixture of the contents of the first package (activator) and second package. The water of the second package can be present alone or admixed with one or more additional ingredients.

The water of the second package preferably contains an oleaginous material emulsified therein in an amount sufficient to form a "with base" or "no-base" relaxer composition. The preferred aqueous emulsion or cream of the second package also preferably contains additional ingredients for the relaxer composition such as a conditioning agent, preservative, fragrance and the like as are typically found in relaxers.

About 2 to about 50 percent of the aqueous portion of the hair relaxer compositions of this invention are preferably comprised of oleaginous materials including mineral oil, petrolatum and mineral jellies. This range is exclusive of the oleaginous materials contained in the modified hectorite clay gellants, discussed hereinafter. Mineral oils useful herein have Saybolt viscosities at 100° F. ranging from about 50 S.U.S. to about 350 S.U.S. and specific gravities at 60° F. of about 0.828 to about 0.895 (0.828/0.895). The materials having Saybolt viscosities of about 50/60 S.U.S. at 100° F. and specific gravities in the ranges 0.828/0.838 at 60° F. are preferred.

Useful petrolatum is also available in several grades based upon both viscosity, melting point and color. The viscosities of these products range between about 50 and about 90 (50/90) S.U.S. at 210° F. Preferably, a colorless or "white" product having a Saybolt viscosity of about 55/75 S.U.S. at 210° F. and melting points in the range of 135°/140° F. and 127°/137° F. are used.

In addition, mineral jellies compounded of white mineral oil, petrolatum and wax can also be used as the oleaginous material in the compositions of this invention. Such materials typically have Saybolt viscosities at 210° F. of about 35/46 S.U.S. preferably about 37/40 S.U.S., U.S.P. melting points of about 97°/120° F., and pour points of about 75°/130° F., preferably of about 110°/120° F.

While the oleaginous materials can be present at about 2 to about 50 weight percent, the percentage actually used in a product depends upon the desired product consistency as is well-known in the formulation of cosmetic creams. Thus, when a very stiff relaxer is desired, petrolatum is preferred over the less viscous mineral oil and mineral jellies. While mineral jellies are themselves mixtures, mixtures such as petrolatum-mineral oil combinations are also useful for varying the viscosity or stiffness of the cream composition. When a thinner or softer cream is desired, the less viscous oleaginous materials are preferred.

The amount of oleaginous material in the relaxer composition is also a function of whether the relaxer is designed to be a "with base" or "no-base" product. A "with base" product typically contains about 2 to about 30 weight percent oleaginous material in the water-containing package, while a "no-base" product typically contains about 20 to about 50 weight percent oleaginous material. The "base" portion or package of a "with base" product typically contains about 70 to about 100 weight percent oleaginous material that is applied to the scalp prior to the application of the relaxer composition.

The water-containing second package of a "with base" product typically contains about 60 to about 70 weight percent water, while the water-containing package of a "no-base" relaxer product typically contains about 40 to about 50 weight percent water in the particularly preferred embodiment in which the water is the continuous phase of the emulsion.

Various emulsifying agents and mixtures thereof are preferably present in the aqueous portion of the hair straightening formulations of this invention. These emulsifiers can include non-ionic, anionic and amphoteric surfactants. Non-ionic emulsifiers can be exemplified by $C_{12}-C_{18}$ fatty alcohols, which can be purchased commercially as such, or individually as is the case for cetyl alcohol, pentadecanol, octadecanol and oleyl alcohol, lanolin and its polyoxyethylene derivatives such as polyoxyethylene (50) lanolin, polyethylene oxide-polypropylene oxide condensates, polyoxyethylene ethers of fatty alcohols such as polyoxyethylene (20) oleyl ether and the like. Additionally, $C_2-C_6$ polyhydroxy compounds such as propylene glycol, glycerin and sorbitol are useful non-ionic emulsifiers of the emulsifying system. Anionic emulsifiers can be illustrated by sodium lauryl sulfate, the stearic acid anion, polyoxyethylene (3) oleyl ether phosphate, and the like. Amphoteric surfactants such as 2-heptadecyl-1-carboxymethyl- 1-(2-hydroxyethyl)-2-imidazolinium chloride sold under the trademark MIRANOL DM by the Miranol Chemical Company, Inc. are particularly useful when cationic conditioning agents are also present in the formulation as is discussed hereinafter.

The use of emulsifying agents at particular concentrations to formulate hair relaxers is known in the art. However, it has been found preferable to use about 2 to about 25 weight percent, and more preferably about 10 to about 20 weight percent, emulsifier in the aqueous portions of either "with base" or "no-base" products.

It is to be understood that all of the above mentioned emulsifying agents need not be used alone, nor in a single formulation, and are preferably used as combinations. When present in the water-containing package of preferred relaxer systems of this invention, the $C_{12}-C_{18}$ fatty alcohols can be present from about 1 to about 20 weight percent, and preferably at about 5 to about 15 weight percent, polyoxyethylene (50) lanolin can be present at about 0.05 to about 12.0 weight percent, and preferably at about 0.5 to about 5 weight percent, and the $C_2-C_6$ polyhydroxy compounds can be present at about 0.01 to about 10.0 weight percent, preferably at about 0.1 to about 5.0 weight percent, all based upon the total weight of the aqueous portion of the relaxer system.

It is noted that the above values for the total amount of emulsifier and the $C_2-C_6$ polyhydroxy compound component of the emulsifier do not include the amount of organic solvent present in the composition from the admixed activator that can be a $C_2$–$C_6$ polyhydroxy compound in particularly preferred practice.

Of the anionic emulsifiers, polyoxyethylene (3) oleyl ether phosphate can be present at about 0.01 to about 3.0 weight percent of the water-containing portion, and more preferably at about 0.05 to about 1.0 weight percent.

The preferred amphoteric emulsifer, 2-heptadecyl-1-carboxymethyl-1-(2-hydroxyethyl)-2-imidazolinium chloride can be present from about 0.10 to about 10 weight percent and preferably at about 0.25 to about 5.0 weight percent of the total composition. This amphoteric emulsifier is particularly useful for hair relaxing compositions that also condition the hair, leaving it soft and manageable as well as straightening it. Water-soluble, quaternary, cationic polymers which modify the hair surface characteristics and thereby improve the hair feel and ease of combing can be used as such hair conditioners or conditioning agents.

The co-assigned U. S. Pat. Nos. 4,175,572 and 4,237,910 disclose hair conditioning compositions which can be used in conjunction with highly alkaline hair straightening compositions. Those patents disclose the use of polydiallyldimethylammonium salts such as the chloride or bromide as the conditioning agent, and that polymeric salt is also useful herein as a conditioner. Polydiallyldimethylammonium chloride can be present in the water-containing emulsion of the second package at about 0.01 to about 10 weight percent as the active polymer, and more preferably at about 0.2 to about 2 weight percent as the active polymer. The above-named amphoteric emulsifier is preferably also present when this conditioner is used.

Polydiallyldimethylammonium chloride is available as an aqueous composition sold under the trademark MERQUAT-100 by E. M. Merck & Co. Details as to its preparation can be found in U.S. Pat. Nos. 3,288,770 and 3,412,091.

Small molecule conditioning agents can also be utilized herein, as can other polymeric conditioners. Exemplary small molecule conditioning agents include stearyldimethylbenzylammonium chloride, dimethyl-di-(hydrogenated tallow)ammonium chloride, and the like. Useful polymeric conditioners include a polymer of hydroxyethyl cellulose reacted with epichlorohydrin and quaternized with trimethylamine sold under the trademark POLYMER JR-125 by Union Carbide Corporation, the polymer formed by the reaction of dimethyl sulfate and a copolymer of vinyl pyrrolidone and dimethylaminoethyl methacrylate sold under the trademark GAFQUAT-734 by GAF Corporation, and the like.

A hydrophobic or lipophilic gellant is preferably included in the second, water-containing package of both a preferred "with base" and a "no-base" relaxer system. These materials provide thickening to the aqueous cream and also to the relaxer composition. A particularly preferred group of lipophilic gellants also provides stability to phase separation of the emulsified relaxer composition for at least about one hour after its preparation, and more preferably for the period of time in which the emulsified relaxer composition is active to relax hair; i.e., about 48 hours.

Particularly preferred lipophilic gellants are organically modified hectorite clays. The organically modified lipophilic clay gelling agents are modified first with a quaternary nitrogen-containing compound and then optionally, by other organic materials. Specific lipophilic gelling agents are comprised of Stearalkonium hectorite or Quaternium-18 [dimethyl-di-(hydrogenated tallow)-ammonium chloride] hectorite, and are sold as powders under the trademarks BENTONE 27 and BENTONE 38, respectively by NL Industries, Inc.

Pregelled oleaginous products containing the above BENTONE gellants are also commercially available and are designated by their manufacturer as mastergels. The mastergels contain about 10 percent of the above BENTONE 27 or 38 gellants along with propylene carbonate and other organic liquids. It is preferred to use the commercially available mastergels as they are known in the art to be difficult to prepare.

The particularly preferred lipophilic hectorite clay gellants are those mastergels comprised of hectorite clays modified with (1) a quaternary nitrogen-containing compound, such as stearalkonium chloride or Quaternium-18, which contains at least one long chain ($C_8$–$C_{20}$) substituent on the quaternary nitrogen atom, (2) propylene carbonate, and (3) a non-polar organic liquid. Examples of such non-polar organic liquids include but are not limited to mineral spirits, mineral oil, glycerides, such as castor oil, a mixture of lanolin oil and isopropyl palmitate, and the like. [Stearalkonium chloride and Quaternium-18 are defined in the *CTFA Cosmetic Ingredient Dictionary*, 2nd ed., published by The Cosmetic Toiletry and Fragrance Association, Inc. at pages 314 and 279, respectively.]

Specific, useful lipophilic gellants which are commercially available from NL Industries, Inc. as mastergels include: BENTONE Gel MIO, comprised of mineral oil, propylene carbonate, and Quaternium-18 hectorite; BENTONE Gel CAO, comprised of propylene carbonate, castor oil and stearalkonium hectorite; BENTONE Gels SS71 and S130 comprised of mineral spirits (ligroin or petroleum spirits having a boiling range of about 318°–400° F.), propylene carbonate and Quaternium-18 hectorite; and BENTONE Gel Lantrol, comprised of propylene carbonate, a mixture of lanolin oil (dewaxed lanolin) and isopropyl palmitate, and stearalkonium hectorite. The above hectorite gellants are not only individually useful in the relaxer compositions of this invention, but may be interchanged, one for the other in a given composition, or mixed together in a composition.

The lipophilic modified hectorites can be present in the aqueous portion of hair relaxing compositions of this invention from about 2 to about 30 weight percent of the total aqueous portion. Below about 2 weight percent, little stability improvement is noted, while above about 30 weight percent, the resulting cream products tend to have congealing points which are too high to allow easy washout. Thus, using less of the hectorite material in the above range leads to softer creams, while using more results in stiffer creams. In particularly preferred practice, the lipophilic modified hectorite is present at about 5 to about 20 weight percent of the relaxer composition.

A "with base" relaxer product typically includes a hydrophilic thickener that is present in the relaxer composition in sufficient quantity to retard dripping. The thickener is preferably present in the aqueous portion of the present relaxer system, and can be used in addition to or to replace the hydrophobic thickener.

A particularly preferred hydrophilic thickener is the gellant manufactured and sold under the trademark BENTONE LT by NL Industries, Inc. BENTONE LT is said by its manufacturer to be a combination of hectorite clay and hydroxyethyl cellulose. Additional useful hectorite clay gellants available from NL Industries, Inc include an amine oxide and hydroxyethyl cellulose modified hectorite clay gellant sold under the trademark BENAQUA, as well as highly purified montmorillonite clays sold under the trademarks BEN-A-GEL and BEN-A-GEL EW. The hydrophilic gellants are preferably present at about 2 to about 30 weight percent of the water-containing package.

More specifically, a "with base" relaxer composition after admixture of the water-containing package and activator is preferably an emulsion that contains about 40 to about 60 weight percent water, about 2 to about 25 weight percent oleaginous material, about 1.5 to about 20 weight percent emulsifiers and about 2 to about 7 weight percent hydrolyzable organic base having a $pK_a$ value of at least about 12. A particularly preferred emulsifier includes about 12 to about 18 weight percent $C_{12}$–$C_{18}$ fatty alcohol, about 0.4 to about 4 weight percent polyoxy ethylene (50) lanolin and about 0.2 to about 3.0 weight percent of the previously mentioned amphoteric emulsifier. About 0.05 to about 8.0 weight percent of a conditioning agent such as polydiallyl-dimethyl- ammonium chloride is also preferably included. Typically, all of the above ingredients except for the hydrolyzable organic base and the polyhydroxy lower alkane are constituents of the second, water-containing package of the relaxer system.

A "no-base" relaxer composition is an emulsion that preferably contains about 30 to about 50 weight percent water, about 15 to about 45 weight percent oleaginous material, about 8 to about 18 weight percent emulsifier, and about 2 to about 7 weight percent hydrolyzable organic base having a $pK_a$ value of at least about 12. Here, a typically useful emulsifier includes about 4 to about 13 weight percent $C_{12}$–$C_{18}$ fatty alcohol, about 0.04 to about 0.8 weight percent polyoxyethylene (3) ether phosphate, about 0.05 to about 8 weight percent of a $C_2$–$C_6$ polyhydroxy compound, and about 0.4 to about 4 weight percent of polyoxyethylene (50) lanolin. When a conditioning agent such as polydiallyldimethylammonium chloride is used in the relaxer composition, the before described amphoteric emulsifier sold under the trademark MIRANOL DM is also preferably present in an amount of about 0.2 to about 5 weight percent.

It is noted that the composition for either a "with base" or a "no-base" relaxer is preferably an emulsion, as that composition is used. The contents of the second package of the relaxer system that includes water are also preferably in the form of an emulsion and when the activator solution is admixed with that emulsion it enters the aqueous phase thereof, producing, a second emulsion which is the relaxer composition that is used to relax hair. That second emulsion preferably contains at least 30 weight percent water and has water as an external or continous phase. The second emulsion is thus preferably an oil-in-water emulsion.

In most cases, the first emulsion is of the same character as the second emulsion with respect to the relationship of its oil and water phases. However, in some cases the addition of the activator solution may cause reversal of the first emulsion from water-in-oil to oil-in-water.

As already noted, it is preferred that the second emulsion, relaxer composition, be stable to breaking for at least one hour after its preparation. More preferably, the second emulsion is stable to breaking through the time at which it is applied to the head to contact the hair.

When compounding a preferred aqueous emulsion or cream, the oleaginous material and nonionic emulsifiers comprise the oil phase of the cream. Those nonionic emulsifiers which are relatively more water soluble, such as polyoxyethylene (50) lanolin and the $C_2$–$C_6$ polyhydroxy compounds such as propylene glycol constitute part of the aqueous phase of the water-containing emulsion of the second package.

All, or a portion of the non-water ingredients of the water-containing package can also be in the activator that is admixed with water to form a "with base" or "no-base" relaxer composition. In this situation, it is preferred to form a dispersion having the organic solvent of the activator and hydrolyzable organic base as the external, continuous phase so that the activator will be readily emulsifiable with the admixed water-containing emulsion when a relaxer composition is prepared. Conversely, it is also possible to have the oleaginous portion, e.g. petrolatum or mineral oil, be the external phase with the organic solvent and hydrolyzable organic base as the internal phase in this activator. Upon admixture with the required water, the phases of the latter dispersion would invert so that the water-organic solvent-hydrolyzable organic base phase is the external phase of the relaxer composition.

In addition to relaxation using the preferred "with base" and "no-base" relaxer systems described hereinbefore, an activator of this invention that contains a hydrolyzable organic base in an organic solvent can also be admixed with water and no other ingredients to form a relaxer composition, as already noted. On-head use of a relaxer composition that contains no oleaginous material or other thickener is not preferred because of the dripping and irritation problems that can result. Such relaxer compositions do, however, relax hair when the relaxer composition contains at least 20 weight percent water, and can be used for comparing the effects of alterations in the activator components and amounts upon relaxation.

For best results, hair relaxation in accordance with this invention is through the sole action of the hydrated, previously free organic base, as described above. The invention, however, does not exclude hair relaxation by the combined action of the hydrated organic base with other relaxing materials, such as sodium or potassium hydroxide, or with guanidium hydroxide generated, as disclosed in the prior art, from the reaction of guanidine carbonate and calcium hydroxide. In the latter case, the full advantages of avoidance of pastiness and maintenance of hair sheen may not be achieved.

Broadly, a relaxer system of this invention is utilized by admixing the contents of the two packages to form a relaxer composition. The relaxer composition so formed is then applied to the head to contact the hair fibers. A longitudinal strain is then exerted on the hair fibers while the hair is in contact with the relaxer composition, as by smoothing the hair into a straightened configuration using a comb back. The contact of relaxer composition and the longitudinal strain are maintained for a time sufficient to relax the hair, usually about 10 to about 45 minutes. The relaxer is then removed from the hair, as by rinsing. The relaxer composition so prepared should be utilized within about 2 days.

When the relaxer system is utilized for a "with base" product, the "base" is applied to contact the scalp prior to the application of the relaxer composition as is illustrated in Example 5.

Specific steps for applying a "no-base" relaxer prepared from the relaxer system of this invention can be found in co-assigned U.S. Pat. No. 4,237,910. The pertinent disclosure of that patent is hereby incorporated by reference.

The present invention utilizes a hydrolyzable organic base in its free base and/or hydrate forms. The free base and hydrate forms of the hydrolyzable organic bases are not readily available in small quantities from commercial sources but are readily prepared in such quantities from commercially available salts. Preparation of the free base and/or hydrate forms of the organic base followed by dissolution thereof in a substantially anhydrous organic solvent forms an activator useful herein. Preparations of activators including guanidine and acetamidine are illustrated hereinafter in Examples 1 and 3, respectively.

The present invention is further illustrated by the Examples which follow.

BEST MODES FOR CARRYING OUT THE INVENTION

EXAMPLE 1: Preparation of Guanidine in Propylene Glycol That Contains Substantially No Free Water An activator solution of this invention containing guanidine $pK_a$ value=13.6) in propylene glycol that contains substantially no free water was prepared as follows:

Guanidine carbonate (519 grams, 2.85 moles as the carbonate) was dissolved in 1000 milliliters of deionized water into which sodium hydroxide (342 grams of a 50 weight percent solution, 4.25 moles) was added with agitation. The resulting solution was stirred for one hour and then placed in a refrigerator for about 18 hours. Calcium hydroxide (148 grams, 2 moles) was added with agitation to the resulting suspension with the agitation continuing for about 1 hour after the addition was complete. The resulting slurry was filtered in convenient portions, with each resulting filter cake being washed with about 100 milliliters of deionized water. The resulting filtrates were combined and stirred until an additional precipitate appeared. The additional precipitate was then removed by filtration.

Anhydrous methanol (about 200 milliliters) was added to the resulting filtrate to produce a new precipitate. That precipitate was removed by filtration. The new resulting filtrate was concentrated under reduced pressure until a further precipitate emerged. Anhydrous methanol (about 200 milliliters) was again added, the resulting solution was again concentrated under reduced pressure until a further precipitate appeared, and the precipitate-containing solution was filtered again. Addition of anhydrous methanol, precipitation, filtration and concentration were repeated twice more after which time no further precipitate was noted. The last solution was taken to apparent dryness under reduced pressure to provide a product that weighed 256 grams.

Karl Fischer assay of the product so prepared indicated that it contained 2.56 weight percent water. High pressure liquid chromatography separated about 7 weight percent urea from the guanidine product. Conductometric titration of the guanidine product using picric acid to precipitate the guanidine present indicated that the product contained about 85 weight percent guanidine.

Elemental analysis indicated the presence of about 2.5 weight percent of a material other than carbon, hydrogen, nitrogen or oxygen, but which was not an inorganic ash. An average of three analyses provided the following data: carbon=19.67 percent; hydrogen=8.22 percent; nitrogen=63.57 percent; and oxygen=6.11 percent. Those data are consistent with a composition that contains about 85 percent guanidine base.

The guanidine (24 grams) so produced was admixed with agitation with propylene glycol (76 grams) to provide an activator solution of this invention that contained a presumed 0.35 moles of guanidine. Analysis of the propylene glycol showed the presence of 0.01 weight percent water. The water content of the activator was therefore about 0.6 parts of water per 100 parts of the activator or about 0.034 moles. This water is believed to hydrate an equimolar amount of guanidine so that the guanidine was present in the activator at about 90 percent as the free base and about 10 percent as the hydrate, guanidinium hydroxide. These calculations indicate that no free water was present.

Example 2: Hair Relaxer Systems

Two hair relaxer systems of this invention were prepared using differing amounts of the guanidine of Example 1. The water-containing portion of the system was an emulsion which was prepared using the components of Table 1, below, as follows:

TABLE 1

| Components | Weight Percent of Water-Containing Composition |
|---|---|
| 1. Petrolatum[1] | 26.35 |
| 2. BENTONE Gel MIO[2] | 12.24 |
| 3. $C_{12}$-$C_{18}$ fatty alcohol[3] | 9.41 |
| 4. Mineral oil[4] | 0.10 |
| 5. Polyoxyethylene (3) oleyl ether phosphate | 0.10 |
| 6. Propylparaben | 0.10 |
| 7. Water, deionized | 42.40 |
| 8. Polydiallyldimethyl[5] ammonium chloride | 3.10 |
| 9. Amphoteric emulsifier[6] | 1.41 |
| 10. Polyoxyethylene (50) lanolin[7] | 3.49 |
| 11. Propylene glycol | 0.51 |
| 12. Methylparaben | 0.25 |
| 13. Imidazolidinyl urea[8] | 0.25 |
| 14. Fragrance | 0.29 |
| | 100.00 |

[1]Petrolatum having a U.S.P. melting point of 135/140° F. and a Saybolt viscosity at 210° F. of 55/75 S.U.S. was used.
[2]A modified hectorite clay gellant sold by NL Industries, Inc.
[3]A fatty alcohol mixture containing cetyl and stearyl alcohols sold under the Trademark TA 1618F by Procter & Gamble was used.
[4]A mineral oil having a Saybolt viscosity at 100° F. of 50/60 S.U.S. and a specific gravity in the range of about 0.828/0.838 at 60° F. was used.
[5]This polymeric conditioner is sold under the trademark MERQUAT-100 by Merck & Co., Inc. as an aqueous composition containing about 40% solids.
[6]The amphoteric emulsifier sold under the trademark MIRANOL DM by Miranol Chemical Company, Inc. was used. This material is sold as an aqueous paste that is about 25% active.
[7]A composition containing 50% active material in water was used.
[8]Imidazolidinyl urea is a preservative sold under the trademark GERMALL 115 by Sutton Laboratories, Inc.

Components 1, 2 and 4 were heated to 80° C. and admixed to form a substantially uniform dispersion. Components 3, 5 and 6 were thereafter admixed with agitation and the resulting composition was maintained at a temperature of 80° C. to form the oil phase of the emulsion.

Components 8-13 were admixed in water (Component 7) with agitation and heating to a temperature of 80° C. to form the water phase of the emulsion.

With both phases at a temperature of about 80° C., the water phase was added slowly to the oil phase with sufficient agitation to form a substantially homogeneous emulsion in which water formed the continuous phase. This emulsion was thereafter cooled to a temperature of 50° C. at which time Component 14 (fragrance) was admixed and dispersed therein. The perfumed emulsion was then cooled to a temperature of about 25° C., homogenized and packaged.

Two half-head comparisons were made using a commercial relaxer prepared from guanidine carbonate and calcium hydroxide as one half-head side (Composition A) and one of two relaxer systems of this invention (Compositions B and C) as the other half-head side. Two models were used.

Upon mixture of the guanidine carbonate solution and water/calcium hydroxide-containing, cream emulsion of the commercial product, relaxer Composition A had a pH value of 13.43 and Brookfield viscosity (Model RVT, spindle Model TE) at 25° C. of about 80,000–90,000 centipoises. Composition A was applied in an amount of 132 grams per half-head and contained about 0.07 moles of guanidine and/or guanidinium hydroxide. Label directions were followed, except for the half-head application, so that the usual salon practices for hair relaxation were followed.

4.4 Grams and 4.8 grams of the guanidine prepared in Example 1 were admixed with about 15.6 grams and about 15.2 grams of the dry propylene glycol of Example 1 to form activators B and C, respectively, of this invention. Activators B and C were then each admixed with 112 grams of the water-containing emulsion of this Example to form the new emulsions that comprise relaxer Compositions B and C, respectively, which were stable to phase separation through their applications in the half-head comparison. Composition B had a pH value of 13.47, a viscosity of about 180,000 under the above conditions and contained about 0.063 moles of guanidine. Composition C had a pH value of 13.42, a viscosity of about 140,000 and contained about 0.069 moles of guanidine. The amount of guanidine in the compositions was determined using the calculations of Example 1. Relaxations using Compositions B and C were performed in a manner indentical to that used for the commercial product to assure a proper comparison.

One half-head comparison showed that Composition B relaxed the hair on its side well, provided hair with good body and sheen, and caused no adverse sensation on the head. Relaxation on the side treated with Composition B was slightly less than that on the side treated with the commercial product.

Composition C relaxed hair on its head side slightly better than did the commercial product on its half-head side. Composition C also rinsed from the hair slightly faster than did the commercial product. The operator preferred the result using Composition C over the result using the commercial product.

Example 3: Hair Relaxer System Containing Acetamidine

Hair relaxation was performed utilizing acetamidine ($pK_a$ value=12.5) in the activator and the water-containing emulsion of Example 2 as the components of the relaxer system, and relaxer composition.

Acetamidine hydrochloride (1.9 grams, 0.02 mole) was dissolved in 75 milliliters of absolute methanol. A 200 milliliter solution containing potassium hydroxide (0.02 mole) in absolute methanol was added slowly to the acetamidine hydrochloride solution with cooling and agitation. The resulting solution was concentrated under reduced pressure to about 75 milliliters and filtered. The precipitate was washed with about 20 milliliters of absolute methanol and the washings were added to the previous filtrate. The combined filtrates were then taken to apparent dryness under reduced pressure to yield the predicted 1.2 grams of a yellow oil. A drop of the oil mixed with an aqueous silver nitrate solution produced a slight haze, indicating that the chloride ion had been substantially removed.

Propylene glycol (3.0 grams) was added to dissolve the thus prepared acetamidine or acetamidinium hydroxide, (1.1 gram), and thereby form an activator of this invention. 4.1 Grams of the activator so formed were then combined with 22.4 grams of a water-containing cream emulsion having the components and amounts of the emulsion of Example 2 to form a relaxer composition.

The acetamidine-containing relaxer composition so formed was then applied to a tress of virgin Negro hair to contact the hair fibers. The thus contacted hair fibers were then placed under a longitudinal strain by smoothing the hair with a comb. The contact and longitudinal strain were maintained for a total of about 25 minutes with additional smoothings every few minutes during that time to maintain the longitudinal strain to relax the hair. The relaxer was thereafter rinsed from the hair with a commercially available shampoo having a pH value of about 5 to about 6, and relaxed hair tress was air dried.

Example 4: Hair Relaxation Using Commercially Available Face Creams as the Water-Containing Portion of a Relaxer System Hair relaxation determinations were carried out using an activator of this invention as one portion of the relaxer system and a commercially available face cream as the water-containing, second, portion of the system. The activator here was made by a method similar to that of Example 1 and is believed to have contained about 3.6 moles per liter of guanidine as the free base and/or hydrate.

Eight commercially available face creams were used individually as the water-containing portion of the relaxer system. The face creams and the relaxer compositions prepared from them are designated herein by the letters D, E, F, G, H, I, J and K.

Four grams of the activator were admixed with 22 grams of each of the face creams to form the relaxer compositions, each of which was applied to a tress of virgin Negro hair. Contact of each relaxer composition with the hair was maintained for about 25 minutes with a longitudinal strain being applied to the tress during that time by smoothing for about 3 seconds per minute. Each tress was thereafter shampooed with the shampoo of Example 3 followed by air drying. The results of these determinations are shown in Table 2 below.

TABLE 2

| | Relaxation Using Activator and Face Cream | |
|---|---|---|
| Face Cream | Degree of Relaxation[1] | Comments |
| D | Some | Note 2 |
| E | Fair | — |
| F | Poor | Note 2 |
| G | Fair | Note 3 |
| H | Poor | Note 2 |

TABLE 2-continued

Relaxation Using Activator and Face Cream

| Face Cream | Degree of Relaxation[1] | Comments |
|---|---|---|
| I | Some | — |
| J | Good | — |
| K | Some | Note 2 |

[1]Relaxation was rated relative to a control tress. In order of decreasing relaxation, the ratings are good, fair, some and poor.
[2]Emulsion separated on mixing.
[3]Emulsion became soupy on mixing.

Examination of the properties (miscibility with water and toluene) of the face cream emulsions and the ingredients listed on their packages indicated that face creams E, G and J were most probably oil-in-water emulsions, while face creams D, F, H, I and K were most probably water-in-oil emulsions. The observed, better relaxation using face creams that are apparently oil-in-water emulsions is in line with the general findings for emulsions created for the present relaxer system that oil-in-water emulsions provide an improved result, particularly where water constitutes at least about 30 weight percent of the relaxer composition.

Example 5: With Base Hair Relaxer

A "with base" relaxer system was prepared which utilized an activator solution that contained 1.3 grams of the guanidine of Example 1 dissolved in 2.7 grams of dry propylene glycol. The entire 4.0 grams of activator was admixed with 22.4 grams of a water-containing cream emulsion whose contents are listed in Table 3, below.

TABLE 3

| Components[1] | Weight Percent of Water-Containing Composition |
|---|---|
| 1. $C_{12}$–$C_{18}$ alcohol | 15.00 |
| 2. BENTONE Gel MIO | 10.00 |
| 3. Petrolatum | 5.00 |
| 4. Water, deionized | 61.65 |
| 5. Polydrallyldimethyl-ammonium chloride | 3.15 |
| 6. Amphoteric emulsifier | 1.40 |
| 7. Polyoxyethylene (50) lanolin | 3.50 |
| 8. Fragrance | 0.30 |
| | 100.00 |

[1]Each of the above components is the same as the identically named component of Example 2.

The components of the water-containing cream emulsion were admixed to form the cream in a manner substantially identical to that utilized in forming the cream of Example 2.

Admixture of the activator and aqueous cream produced an emulsion that did not separate one hour after its preparation.

The admixed relaxer composition was applied to a tress of virgin Negro hair in an amount sufficient to adequately cover the fibers and contact the hair with the relaxer composition. The hair-relaxer composition contact was maintained for a period of 25 minutes with occasional smoothing of the treated tress during that time to provide strain to the relaxing hair fibers.

The tress was then shampooed as described in Example 3, rinsed and dried. Good relaxation was observed.

Example 6: Activators Containing Various Organic Alcoholic Solvents

Activators were prepared using the guanidine of Example 1 in alcoholic solvents other than propylene glycol, as well as in propylene glycol utilized at one-half and twice the relative amount used in the activator of Example 2. Each activator so prepared was then mixed with 22.4 grams of a water-containing cream having the composition of the cream of Example 2 to prepare relaxer compositions of this invention. Each relaxer composition was then applied to a tress of virgin Negro hair and maintained in contact with that hair for a period of 25 minutes. The relaxer composition was removed with a shampoo having an acidic pH value, and the tresses were rinsed with tap water and air dried. The hair of each of the treated tresses was relaxed by each of the treatments. The solvents used and their amounts are shown in Table 4 below.

TABLE 4

| Solvent | Activators[1] Amount (grams) |
|---|---|
| Glycerin | 3.04 |
| Pluronic L-121[2] | 3.04 |
| Benzyl alcohol | 3.04 |
| Methanol | 3.04 |
| 2-Propanol | 3.04 |
| Iso-cetyl alcohol-[3] Methanol (5:6 by weight) | 3.3 |
| Monoethanolamine | 3.04 |
| Propylene glycol | 1.50 |
| Propylene glycol | 6.08 |

[1]Each activator also contained 0.96 grams of the guandine prepared in Example 1. Each activator therefore contained about 0.01 moles of guanidine, based upon the analytical data of Example 1.
[2]PLURONIC L-121 is a trademark for a hydroxyl-terminated polyoxyethylene-polyoxypropylene-polyoxyethylene block polymer described previously and sold by BASF-Wyandotte. The activator produced with this organic solvent was thickened and gel-like, but it was quite effective for relaxing hair when mixed with the aqueous cream.
[3]Iso-cetyl alcohol does not, itself, dissolve the guanidine. Addition of six parts absolute methanol to five parts iso-cetyl alcohol and the guanidine resulted in an effective activator having a single phase.

The above-described results amply demonstrate the effectiveness of the various alcoholic organic solvents utilized for each of the activators.

Example 7: Comparative Reflectance

The reflectances of hair tresses relaxed according to this invention were compared to the reflectances of tresses relaxed using a commercially available relaxer composition prepared from guanidium carbonate and calcium hydroxide.

Three hair tresses were utilized for each condition. Brown, virgin European hair tresses (DeMeo Brothers, New York, New York) were utilized. Each tress was approximately five inches long and weighed about 2 grams.

Contrast Ratio and Degree of Lightness were measured before and after relaxation using a reflectance goniophotometer. A discussion of the principles involved in measuring light reflectance from hair may be found in Stamm et al., *Journal Society of Cosmetic Chemists*, Vol. 28, 571–609 (1977).

Contrast Ratio is the ratio of (a) light intensity measured at an angle 90° to the angle of incidence of the light beam to (b) the intensity of light measured at 60° to the angle of incidence. Contrast Ratio is thus a ratio of the peak reflectance of light from the hair to a lesser reflectance value that is measured at a constant angle from the peak reflectance, 30°, and at a point near the reflectance minimum. This ratio thereby provides a relative measure for the luster or sheen of the tress.

Degree of Lightness measures the relative lightness of color of the hair sample and is useful in determining whether a given treatment has changed the hair color. An increase in Degree of Lightness values indicates a lightening of the tress color. Degree of Lightness data are obtained from the reflectance of the tress at an angle of 60° from the angle of incidence of the light beam. Thus, each data point for Degree of Lightness is the denominator utilized in calculating Contrast Ratio for a particular determination.

A recording goniophotometer that provided a beam of incandescent light at an angle of 45° to a substantially flat, horizontal tress was used for these measurements. A selenium photocell, whose response to light is similar to that of a human eye, mounted to a motorized arm having a total scan of about 60° was used to measure the reflectances. Output from the photocell was fed to a strip chart recorder whose rate of paper advancement was attuned to the photocell scan so that one inch of paper advance corresponded to 30° of scan. Data were collected directly from the recorded chart by measuring the height of the peak reflectance on the curve produced, and the height on the curve one inch in a horizontal direction (30°) from the point of peak reflectance.

Each tress used was laid flat on a horizontal surface for measuring the reflectances, with care being taken to arrange the hair fibers in parallel relation to each other. Each measurement was made two times, with both sides of each tress being measured twice. The mean of the four measurements so made for a given tress served as the value for that tress.

Tresses treated according to this invention were treated with a relaxer composition that was prepared from an activator containing 1.2 grams of the guanidine of Example 1 dissolved in 3.8 grams of propylene glycol and used 28 grams of an aqueous cream having a composition substantially identical to the aqueous cream of Example 2. Each of the three tresses was treated with 10 grams of the relaxer composition so prepared for a period of 20 minutes. The relaxer was rinsed out, shampooed twice with a low pH value shampoo and then dried with a hair dryer.

The commercially available guanidinium carbonate-calcium hydroxide relaxer was prepared according to package instructions. The three tresses were treated with 10 grams each of the relaxer so prepared, using the above conditions.

Analysis of the data showed a statistically significant 66 percent increase at the 95 percent confidence level in the Contrast Ratio (sheen) for tresses treated according to this invention and a statistically insignificant decrease for the tresses treated with the commercial product. Changes in the Degree of Lightness for all tresses were not statistically significant. The Student's t-test and the f-test were utilized in analyzing the data. The data from these measurements is shown in Table 5 below.

TABLE 5

| Treatment | Reflectance Measurements* (Average of Mean Values) | |
|---|---|---|
| | Before Treatment Contrast Ratio | Treatment |
| This invention | 9.25 | 15.34 |
| | (1.07) | (3.52) |

TABLE 5-continued

| Treatment | Reflectance Measurements* (Average of Mean Values) | |
|---|---|---|
| | Before Treatment Contrast Ratio | Treatment |
| Commercial product | 7.65 (2.76) | 7.05 (1.59) |
| DEGREE OF LIGHTNESS | | |
| This invention | 1.49 (0.30) | 1.05 (0.38) |
| Commercial product | 1.72 (0.50) | 1.81 (0.32) |

*Parenthesized numbers are standard deviations.

The cause of the improvement in sheen shown by the above data for relaxation according to this invention over relaxation using a commercially available guanidinium carbonate-calcium hydroxide relaxer is not known.

Example 8: Relaxation Using Dilute Relaxer Compositions

A relaxer composition was prepared by admixing 1.92 grams of the guanidine of Example 1 (85% pure) with 6.08 grams of dry propylene glycol to form an activator. The activator so prepared (8.0 grams) was then admixed with 44.8 grams of a water-containing cream emulsion having a composition substantially identical to the emulsion of Example 2 to form a relaxer composition.

The relaxer composition had a pH value of 13.71 and contained approximately, 0.03 grams of guanidine per gram of composition, based upon the calculations of Example 1. This composition will be hereinafter referred to as Composition L.

Ten grams of composition L were admixed with 37.8 grams of deionized water to form a new relaxer composition which will hereinafter be referred to as Composition M. Composition M contained about 0.007 grams of guanidine per gram of composition and had a pH value of 12.95.

Ten grams of Composition L were admixed with 417.8 grams of deionized water to form another new relaxer composition which will hereinafter be referred to as Composition N. Composition N contained about 0.0007 grams of guanidine per gram of composition and had a pH value of 11.83.

Each of Compositions L, M and N was then utilized to relax a tress of virgin Negro hair, each of which tresses contained about 0.2 grams of hair. These compositions were applied at approximately the same ratio of relaxer composition to hair that is used in relaxing a full head of hair, e.g. about 5 grams of relaxer per gram of virgin Negro hair.

Contact of the relaxer composition with the hair was maintained for varying times, as is shown in Table 6, below. The relaxer compositions were then washed from the tresses using the low pH-value shampoo of Example 3, and the tresses were dried. The amount of relaxation for each of the three conditions is also shown in Table 6.

TABLE 6

| Relaxer Composition | pH Value | Relaxation Time (Minutes) | Relative Relaxation |
|---|---|---|---|
| L | 13.71 | 25 | Good |
| M | 12.95 | 60 | Fair |

TABLE 6-continued

| Relaxer Composition | pH Value | Relaxation Time (Minutes) | Relative Relaxation |
|---|---|---|---|
| N | 11.83 | 90 | Fair |

The data in Table 6 illustrate that relaxation can be accomplished at a pH value as low as 11.83.

From the above dilutions, one can calculate the approximate amount of guanidine that would be in a relaxer product for use on a whole head, which product typically weighs about 264 grams. Thus, translated to 264 grams for a whole head condition, relaxer composition L would have contained 0.13 moles of guanidine, relaxer composition M would have contained 0.03 moles, and relaxer N would have contained 0.003 moles.

The present invention has been described generally and with respect to preferred embodiments. It will be clear to those skilled in the art that modifications and/or variations of the disclosed methods and compositions can be made without departing from the scope of the invention set forth herein. The invention is defined by the claims that follow.

What is claimed is:

1. A hair relaxer system in at least two packages comprising:
   (a) a first package containing a substantially water-free activator that includes a hydrolyzable organic base having a $pK_a$ value of at least 12 that is dissolved in an organic solvent, said organic base being present in free base form in an amount of at least 0.05 moles, sufficient to relax hair and in molar-excess over free and combined water of at least 70 mole percent, said organic solvent being immiscible with petrolatum at a temperature of 25° C.; and
   (b) a second package containing water; the contents of said first and second packages when admixed forming a relaxer composition having a pH value of at least 12, and containing at least 20 weight percent water.

2. The hair relaxer system according to claim 1 wherein said hydrolyzable base is selected from the group consisting of guanidine, guanidine substituted with 1 to 5 substituents selected from the group consisting of lower alkyl, carboxy lower alkyl, hydroxy lower alkyl, amino and lower alkyl substituted amino groups, acetamidine, acetamidine substituted on the carbon atom with a substituent selected from the group consisting of lower alkyl, amino, lower alkyl substituted amino groups, and mixtures thereof.

3. The hair relaxer system according to claim 1 wherein said organic solvent is a polyhydroxy lower alkane.

4. The hair relaxer system according to claim 1 wherein said second package contains an oleaginous material selected from the group consisting of mineral oil, petrolatum, mineral jelly and mixtures thereof emulsified with said water.

5. The hair relaxer system according to claim 4 wherein said second package contains an oil-in-water emulsion.

6. The hair relaxer system according to claim 5 wherein said oil-in-water emulsion contains at least 30 weight percent of water.

7. The hair relaxer system according to claim 1 wherein admixture of the contents of said first and second packages forms a relaxer composition having a pH value of at least 13.

8. A hair relaxer system in at least two packages comprising:
   (a) a first package containing a substantially water-free activator that includes a hydrolyzable organic base having a $pK_a$ value of at least 12 that is dissolved in a polyhydroxy lower alkane, said organic base being present in free base form in an amount of at least 0.05 moles, sufficient to relax hair and in molar excess over free and combined water of at least 70 mole percent; and
   (b) a second package containing an oleaginous material selected from the group consisting of mineral oil, petrolatum, mineral jelly and mixtures thereof emulsified in water;
   the contents of said first and second packages when admixed forming a relaxer composition having a pH value of at least about 13, and containing at least 30 weight percent water.

9. The hair relaxer system according to claim 8 wherein said organic base is guanidine.

10. The hair relaxer system according to claim 8 wherein said organic base is acetamidine.

11. The hair relaxer system according to claim 8 wherein said polyhydroxy lower alkane is propylene glycol.

12. The hair relaxer system according to claim 8 wherein admixture of the contents of said first and second packages forms a relaxer composition containing about 40 to 60 weight percent water.

13. The hair relaxer system according to claim 8 wherein admixture of the contents of said first and second packages forms a relaxer composition containing about 30 to about 50 weight percent water.

14. The relaxer system according to claim 13 wherein said relaxer composition emulsion is stable to phase separation at 25° C. for at least one hour after formation.

15. A hair relaxer system in at least two packages comprising:
   (a) a first package containing a substantially water-free activator that includes guanidine dissolved in propylene glycol, said guanidine being present in the free base form in an amount of at least 0.05 moles, sufficient to relax hair, said package having a total content of free and combined water not higher than 5 weight percent of the weight of guanidine therein; and
   (b) a second package containing an oleaginous material selected from the group consisting of mineral oil, petrolatum, mineral jelly and mixtures thereof emulsified in water; the contents of said first and second packages when admixed forming a relaxer composition emulsion having a pH value of at least about 13, about 30 to about 50 weight percent water and being stable to phrase separation at 25° C. for at least one hour after formation.

16. The hair relaxer system of claim 15 wherein said second package includes at least one emulsifier of the group consisting of non-ionic, anionic and amphoteric surfactants.

17. The hair relaxer system of claim 16 wherein said emulsifier is non-ionic and comprises at least one fatty alcohol having 12 to 18 carbon atoms.

18. The hair relaxer system of claim 15 wherein said second package includes a polydiallyldimethylammonium salt as a conditioner.

19. The hair relaxer system of claim 15 wherein said second package includes an organically modified hectorite clay as a lipophilic gellant.

20. A method of relaxing hair comprising the steps of:
providing the relaxer system of claim 1;
admixing the contents of the packages of said system to form said relaxer composition;
applying said relaxer composition to contact the hair;
exerting a longitudinal strain on the hair fibers while said hair is in contact with said relaxer composition; and
maintaining said contact and said longitudinal strain for a time sufficient to relax said hair.

21. A method of relaxing hair comprising the steps of:
providing the relaxer system of claim 8;
admixing the contents of the packages of said system to form said relaxer composition;
applying said relaxer composition to contact the hair;
exerting a longitudinal strain on the hair while said hair is in contact with said relaxer composition; and
maintaining said contact and said longitudinal strain for a time sufficient to relax said hair.

22. A method of relaxing hair comprising the steps of:
applying an oleaginous material selected from the group consisting of mineral oil, petrolatum, mineral jelly and mixtures thereof to contact the scalp;
providing the relaxer system of claim 12;
admixing the contents of the packages of said system to form said relaxer composition;
applying said relaxer composition to contact the hair after said oleaginous material has been applied to the scalp;
exerting a longitudinal strain on the hair while said hair is in contact with said relaxer composition; and
maintaining said contact and said longitudinal strain for a time sufficient to relax said hair.

23. A method of relaxing hair comprising the steps of:
providing the relaxer system of claim 15;
admixing the contents of the packages of said system to form said relaxer composition;
applying said relaxer composition to contact the hair;
exerting a longitudinal strain to the hair while said hair is in contact with said relaxer composition; and
maintaining said contact and said longitudinal strain for a time sufficient to relax said hair.

24. A method of forming a hair relaxer composition comprising the steps of:
providing the relaxer system of claim 8; and
admixing the contents of the packages of said system to form said relaxer composition.

25. A method of forming a hair relaxer composition comprising the steps of:
providing the relaxer system of claim 1; and
admixing the contents of the packages of said system to form said relaxer composition.

26. A method of forming a hair relaxer composition comprising the steps of:
providing the relaxer system of claim 15; and
admixing the contents of the packages of said system to form said relaxer composition.

27. An activator for a hair relaxing composition comprising a hydrolyzable organic base having a $pK_a$ value of at least 12 that is dissolved in a polyhydroxy lower alkane, said organic base being present in free base form in an amount of at least 0.05 moles and sufficient to relax hair, and said activator being substantially free of water and said organic base being in molar excess over free and combined water of at least 70 mole percent.

28. The activator according to claim 27 wherein said hydrolyzable base is selected from the group consisting of guanidine, guanidine substituted with 1 to 5 substituents selected from the group consisting of lower alkyl, carboxy lower alkyl, hydroxy lower alkyl, amino and lower alkyl substituted amino groups, acetamidine, acetamidine substituted on the carbon atom with a substituent selected from the group consisting of lower alkyl, amino, lower alkyl substituted amino groups, and mixtures thereof.

29. The activator according to claim 27 wherein said polyhydroxy lower alkane is propylene glycol.

30. The activator according to claim 27 wherein said hydrolyzable organic base is guanidine.

31. An activator for a hair relaxing composition comprising a substantially water-free solution of guanidine free base dissolved in propylene glycol, said activator when admixed with water forming a relaxer composition having a pH value of at least 12, containing an amount of guanidine of at least 0.05 moles, which, amount is effective to relax hair, said substantially water-free solution being one in which the total content of free and combined water is not higher than 5 weight percent of the weight of guanidine free base therein.

* * * * *